United States Patent [19]

Hamprecht

[11] Patent Number: 5,214,143
[45] Date of Patent: May 25, 1993

[54] 2-AMINO-4-FLUOROALKOXY-1,3,5-TRIAZINES AND THE PREPARATION THEREOF

[75] Inventor: Gerhard Hamprecht, Weinheim, Fed. Rep. of Germany

[73] Assignee: BASF Aktiengesellschaft, Ludwigshafen, Fed. Rep. of Germany

[21] Appl. No.: 733,844

[22] Filed: Jul. 22, 1991

[30] Foreign Application Priority Data

Aug. 3, 1990 [DE] Fed. Rep. of Germany ....... 4024761

[51] Int. Cl.$^5$ ................. C07D 251/46; C07D 251/42
[52] U.S. Cl. .................................................. 544/194
[58] Field of Search ........................................... 544/194

[56] References Cited

U.S. PATENT DOCUMENTS

| | | | |
|---|---|---|---|
| 4,443,243 | 4/1984 | Fory et al. | 544/211 |
| 4,515,626 | 5/1985 | Szczepanski | 71/93 |
| 4,518,776 | 5/1985 | Meyer et al. | 544/211 |
| 4,542,216 | 9/1985 | Pfluger | 544/320 |
| 4,579,583 | 4/1986 | Fory et al. | 71/92 |
| 4,816,064 | 3/1989 | Konno et al. | 71/93 |
| 4,831,138 | 5/1989 | Lachhein | 544/320 |

FOREIGN PATENT DOCUMENTS 1223591 6/1987 Canada.
0378089 7/1990 European Pat. Off..

OTHER PUBLICATIONS

Chemical Abstracts, Band 112, 72315K, (1990), No. 9, 26 Feb. 1990, Columbus, Ohio, U.S.A.; Morishige et al.
Chemical Abstracts, Band 109, 88185s, (1988), No. 11, 12 Sep. 1988, Columbus, Ohio, U.S.A.
Rico, I et at., Tet. Lett, vol. 22, 323, 1981.
McElvain, S. et al J.A.C.S. 64, 1826, 1942.
McElvain, S. et al J.A.C.S. 71, 40, 1949.
Kloter, G. et al J.A.C.S. 101, 347, 1979.
The Journal of the American Chemical Society, vol. 83, pp. 4860–4869, Dec. 5, 1961, "Communications to the Editor" Dickens et al.
Tsunoda et al, Chemical Abstracts, vol. 87, (1977), p. 486, 87:53396m.

*Primary Examiner*—John M. Ford
*Attorney, Agent, or Firm*—Oblon, Spivak, McClelland, Maier & Neustadt

[57] ABSTRACT

2-Amino-4-fluoroalkoxy-1,3,5-triazines of the formula I

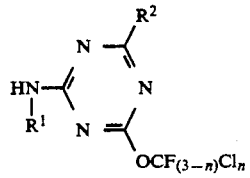

where $R^1$ is hydrogen, alkyl, alkenyl, alkynyl; $R^2$ is hydrogen, halogen, haloalkyl, trifluoromethoxy or chlorodifluoromethoxy and n is 0 or 1 are prepared as described.

7 Claims, No Drawings

2-AMINO-4-FLUOROALKOXY-1,3,5-TRIAZINES AND THE PREPARATION THEREOF

The present invention relates to novel 2-amino-4-fluoroalkoxy-1,3,5-triazines of the formula I

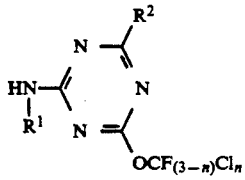

where
$R^1$ is hydrogen, $C_1$-$C_4$-alkyl, $C_3$-$C_6$-alkenyl or $C_3$-$C_4$-alkynyl;
$R^2$ is hydrogen, halogen, $C_1$-$C_4$-haloalkyl, trifluoromethoxy or chlorodifluoromethoxy and
n is 0 or 1.

The present invention also relates to a process for preparing the 1,3,5-triazines I by reacting 2-halo-4-fluoroalkoxy-1,3,5-triazines with amines.

The 1,3,5-triazines I are valuable intermediates for organic syntheses, especially for preparing crop protection agents, e.g. herbicidal sulfonylurea derivatives.

There are many indications in the literature that fluoroalkyl and fluoroalkoxy groups are equivalent to halogen in that they have similar electronic properties. pKa measurements (Proc. Natl. Acad. Sci. U.S.A. 134 (1960) 1207, J. Am. Chem. Soc. 83 (1961) 4860) demonstrate that, for example, fluoroalkoxy groups attract electrons by induction and, conversely, also act as electron donors because of their resonance capacity. Taking all the effects together, the trifluoromethoxy group is in fact more strongly deactivating than the halogens, so that the term super-halogens is also used (J. Am. Chem. Soc. 83 (1961) 4860). This applies in the same way to their ability to be substituted by nucleophiles. Chemical Abstracts 87, 53396 demonstrates, for example, that when 2,4-bis(trichloromethyl)-6-trifluoromethyl-1,3,5-triazine is stirred with basic amines in benzene there is replacement of both haloalkyl groups. The ability of the trifluoromethoxy radical to act as leaving group is also utilized, for example, in sugar chemistry (CA. 105, 115325; 107, 96978).

These facts explain why to date no process for preparing 2-amino-4-fluoroalkoxy-1,3,5-triazines has been disclosed. The only disclosure has been in the pyrimidine series where 4-difluoromethoxy-2-halo compounds were converted with toxic methyl mercaptan into 2-methylthiopyrimidines which were then oxidized to 2-methylsulfonyl derivatives, followed by nucleophilic displacement with amine (U.S. Pat. No. 4,542,216).

We have now found that the novel 2-amino-4-fluoroalkoxy-1,3,5-triazines of the formula I

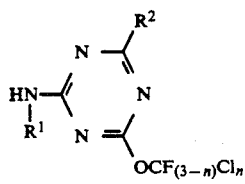

where $R^1$, $R^2$ and n have the abovementioned meanings, are obtained in an advantageous manner when 2-halo-1,3,5-triazines of the formula II

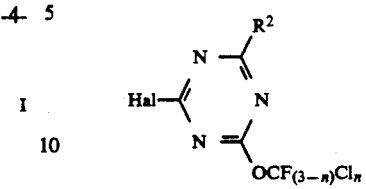

where Hal is fluorine, chlorine, bromine or iodine, and $R^2$ and n have the abovementioned meanings, are reacted with an amine of the formula III

H—NH—$R^1$   III where $R^1$ has the abovementioned meaning.

The reaction of 2,4-difluoro-6-trifluoromethoxy-1,3,5-triazine with ammonia can be represented as follows:

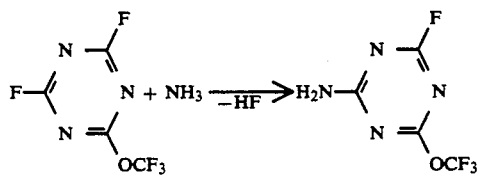

The process provides in a straightforward and economic manner novel 2-amino-4-fluoroalkoxy-1,3,5-triazines in high yield and purity. Unexpectedly, fluoroalkoxy groups are not replaced under the reaction conditions. In view of the prior art, all these advantageous properties are surprising.

Preferred products I and, accordingly, preferred starting materials II are those where $R^1$ is hydrogen, $C_1$-$C_4$-alkyl such as methyl, ethyl, n-propyl, i-propyl, n-butyl, sec-butyl, i-butyl, tert-butyl; $C_3$-$C_4$-alkenyl such as 2-propenyl, 2-methylethenyl, 2-butenyl, 3-butenyl, 1-methyl-2-propenyl or 2-methyl-2-propenyl; $C_3$-$C_4$-alkynyl such as propargyl, 2-butynyl, 3-butynyl or 1-methyl-2-propynyl; $R^2$ is hydrogen, fluorine, chlorine, bromine, trichloromethyl, dichlorofluoromethyl, chlorodifluoromethyl, trifluoromethyl, 1,1-dichloro-2,2,2-trifluoroethyl, 1,1,2,2,2-pentafluoroethyl or 1,1,2,2,2-pentachloroethyl, also trifluoromethoxy or chlorodifluoromethoxy, and n is 0 or 1.

Among the amines which can be employed, the following should be mentioned: ammonia, methylamine, ethylamine, n-propylamine, isopropylamine, n-butylamine, isobutylamine, sec-butylamine, tert-butylamine, 2-propenylamine, 2-methylethenylamine, 2-butenylamine, 3-butenylamine, 1-methyl-2-propenylamine, 2-methyl-2-propenylamine, propargylamine, 2-butynylamine, 3-butynylamine and 1-methyl-2-propynylamine.

The 2-halo-1,3,5-triazines II can be reacted with the amines III in an aprotic polar solvent at from $-80°$ to $40°$ C., either employing the amine III in an excess relative to II or using an additional organic base.

The reaction of the 2-halo-1,3,5-triazine II with the amine III can be carried out in the absence or, advantageously, in the presence of a solvent. Particularly suitable solvents are the following: ethers such as methyl tert-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters such as ethyl acetate, n-butyl acetate and isobutyl acetate, and chlorohydrocarbons such as methylene chloride, 1,1,2,2-tetrachloroethane, 1,1-dichloroethylene, 1,2-dichloroethane, chlorobenzene, 1,2-dichlorobenzene and 1-chloronaphthalene, and mixtures thereof.

The solvent is expediently used in an amount of from 100 to 2000%, preferably 400 to 1200%, of the weight of the starting material II.

It is advantageous to add from 1.8 to 2.5, in particular 1.95 to 2.2, mole equivalents of the amine III, based on the starting material II, over the course of from 0.5 to 2 hours to a mixture of starting material II and one of the abovementioned solvents at $-80°$ to $40°$ C., preferably $-70°$ to $25°$ C., to stir until the reaction is complete (after about 3 hours) and then to warm to $25°$ C. for the working up.

If only approximately the stoichiometric amount of the amine III is used, it is expedient to use an additional organic base in order to trap the hydrogen halide which is formed. Suitable bases for this purpose are trimethylamine, triethylamine, ethyldiisopropylamine, triisopropylamine, N,N-dimethylaniline, N,N-dimethylcyclohexylamine, N-methylpyrrolidine, pyridine, quinoline, $\alpha$-, $\beta$- and $\gamma$-picoline, 2,4- and 2,6-lutidine and triethylenediamine. It is generally sufficient to add from 0.9 to 1.1 equivalents of the base relative to the starting material II.

The reaction can be carried out under atmospheric or superatmospheric pressure, continuously or batchwise.

Working up can be carried out in a conventional manner, e.g. the reaction mixture is extracted with water to remove the salts, and the organic phase is dried and purified by, for example, chromatography. However, it is also possible to concentrate the organic phase directly and to stir the residue with a solvent.

With a view to their further processing to give herbicidal substances, e.g. sulfonylurea derivatives, the following 1,3,5-triazines of the formula I are particularly preferred:
2-amino-4-chloro-6-trifluoromethoxy-1,3,5-triazine,
2-amino-4-fluoro-6-trifluoromethoxy-1,3,5-triazine,
2-amino-4-chloro-6-chlorodifluoromethoxy-1,3,5-triazine,
2-amino-4-fluoro-6-chlorodifluoromethoxy-1,3,5-triazine,
2-amino-4,6-bis-trifluoromethoxy-1,3,5-triazine,
2-amino-4,6-bis-chlorodifluoromethoxy-1,3,5-triazine,
2-amino-4-trifluoromethoxy-6-trifluoromethyl-1,3,5-triazine,
2-amino-4-chlorodifluoromethoxy-6-trifluoromethyl-1,3,5-triazine,
2-methylamino-4-chloro-6-trifluoromethoxy-1,3,5-triazine,
2-methylamino-4-fluoro-6-trifluoromethoxy-1,3,5-triazine,
2-methylamino-4-chloro-6-chlorodifluoromethoxy-1,3,5-triazine,
2-methylamino-4-fluoro-6-chlorodifluoromethoxy-1,3,5-triazine,
2-methylamino-4,6-bis-trifluoromethoxy-1,3,5-triazine,
2-methylamino-4,6-bis-chlorodifluoromethoxy-1,3,5-triazine,
2-methylamino-4-trifluoromethoxy-6-trifluoromethyl-1,3,5-triazine,
2-methylamino-4-chlorodifluoromethoxy-6-trifluoromethyl-1,3,5-triazine,
2-allylamino-4-chloro-6-trifluoromethoxy-1,3,5-triazine,
2-allylamino-4-fluoro-6-trifluoromethoxy-1,3,5-triazine,
2-allylamino-4-chloro-6-chlorodifluoromethoxy-1,3,5-triazine,
2-allylamino-4-fluoro-6-chlorodifluoromethoxy-1,3,5-triazine,
2-allylamino-4,6-bis-trifluoromethoxy-1,3,5-triazine,
2-allylamino-4,6-bis-chlorodifluoromethoxy-1,3,5-triazine,
2-allylamino-4-trifluoromethoxy-6-trifluoromethyl-1,3,5-triazine,
2-allylamino-4-chlorodifluoromethoxy-6-trifluoromethyl-1,3,5-triazine.

The 2-halo-1,3,5-triazines required as starting materials II can be prepared by the process described in Japanese Laid-Open Application 17 039 ('63), Chemical Abstracts 60, 2986 d in tetrachloromethane. However, a considerably more advantageous process is that described in German Application P 40 24 755 (O.Z. 0050/41798) of the same date, which is represented by the following scheme:

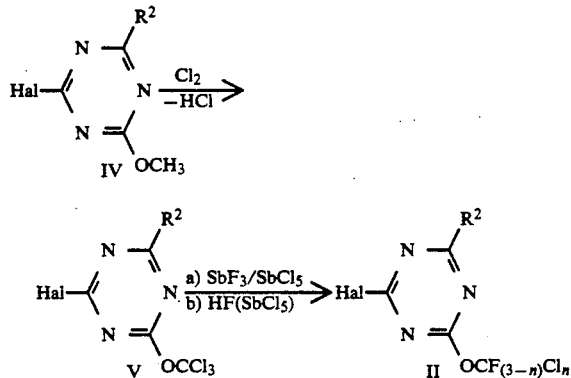

The chlorination of the methoxy-1,3,5-triazine IV with chlorine to give the trichloromethoxy-1,3,5-triazine V is carried out, for example, at from 100° to 180° C.

Suitable for the chlorination are elemental chlorine or chlorine-releasing substances such as sulfuryl chloride or phosphorus pentachloride. Chlorine can also be prepared in situ by oxidation of hydrogen chloride, for example with hydrogen peroxide.

The chlorination can be carried out in the presence of an inert solvent, for example a chlorohydrocarbon such as chlorobenzene, 1,2-, 1,3- or 1,4-dichlorobenzene, a nitro compound such as nitrobenzene, a carboxylic acid such as acetic acid or propionic acid, an anhydride such as acetic anhydride, an acid chloride such as chloroacetyl chloride, $\alpha$-chloro-propionyl chloride or $\alpha,\alpha'$-dichloropropionyl chloride, an inorganic acid halide such as phosphorus trichloride or phosphorus oxychloride or, preferably, without solvent in a melt of the starting material.

The reaction rate may be increased by the use of a radical initiator, those suitable being irradiation with light, preferably UV light, or addition of $\alpha,\alpha'$-azoisobutyronitrile, expediently in an amount of from 0.2 to 7 mol % based on the starting material. The reaction rate can also be increased by adding a catalyst; suitable for this is phosphorus pentachloride, expediently in an amount of from 0.5 to 7 mol % based on starting material IV. In this case, the starting material IV and catalyst are mixed and then the chlorination is started. In place of phosphorus pentachloride it is also possible to add starting components which form the latter under the reaction conditions, e.g. phosphorus trichloride or yellow phosphorus, and then to start the chlorination.

Starting material IV can be reacted with chlorine in approximately the stoichiometric amount or, preferably, in excess, advantageously from 3.1 to 11, in particular 3.3 to 5, moles of chlorine per methoxy equivalent in the starting material IV. The reaction is carried out at from 100° to 180° C., advantageously from 120° to 150° C., under atmospheric or superatmospheric pressure, continuously or batchwise.

If the chlorination is carried out under 1 bar, it is expedient to use from 3.3 to 5 moles of gaseous chlorine per methoxy equivalent in the starting material IV, which corresponds to a chlorine conversion of from 91 to 60%. The chlorine conversion can be increased by appropriate measures, e.g. by use of moderate pressure, expediently from 1 to 10 bar, or by using a bubble column. It is advantageous to allow the gaseous chlorine to stay in contact with the organic phase for as long as possible by, for example, vigorously stirring the latter or forcing the chlorine to pass through a thick layer of the organic phase. The reaction generally takes from about 0.5 to 12 hours.

The procedure in a preferred embodiment of the process is to pass the required amount of gaseous chlorine into the vigorously stirred liquid starting material IV over the course of from 0.5 to 12 hours, preferably 1 to 10 hours, starting at from 120° to 130° C. and raising the temperature continuously, where appropriate by utilizing the exothermic nature of the reaction, until it is at from 135° to 150° C. toward the end of the reaction. It is obvious that for larger batches the exothermic nature of the reaction must be taken into account by external cooling or suitable metering of the chlorine; when the reaction subsides the cooling bath is removed and, where appropriate, heat is then applied.

The products can be worked up and isolated in a conventional manner. For example, residual hydrogen chloride, chlorine or catalyst can be driven out of the hot organic phase using an inert gas; this leaves behind a high yield of crude product which is already rather pure. It can be further purified by distillation or chromatography, or else used immediately for further reactions.

The halogen replacement on the trichloromethoxy-1,3,5-triazine V is carried out, for example, at from 0° to 180° C.

Suitable for the halogen replacement are antimony trifluoride in the presence or absence of catalytic amounts of an antimony(V) salt, e.g. antimony(V) chloride or hydrogen fluoride. It is expedient to use an excess of from 1 to 200, preferably 5 to 25, mol % of antimony trifluoride per trichloromethyl equivalent. The catalytic amount of antimony(V) salt is from 1 to 20, preferably 5 to 18, mol % per trichloromethyl equivalent. The starting material V is preferably metered at from 90° to 130° C. into the mixture containing the agent for halogen replacement, and the mixture is then heated at from 110° to 180° C. for from 10 to about 240 minutes. Subsequent working up is by distillation.

However, the reaction can also be carried out continuously, adding the starting material V at from 110° to 180° C. over the course of from 10 to about 240 minutes and, at the same time, removing the lower boiling product II by distillation under reduced pressure. Traces of antimony salts which are carried over can be removed by extraction with concentrated hydrochloric acid.

The halogen replacement remains at the chlorodifluoromethoxy stage if no antimony(V) salt is used for catalysis or if only small amounts, e.g. from 0.5 to 5 mol %, are employed and the amount of antimony trifluoride is reduced to from 60 to 90 mol % per trichloromethyl equivalent.

The halogen replacement can also be carried out with hydrogen fluoride, in place of antimony trifluoride, at from 0° to 150° C., preferably 40° to 120° C. For this purpose, an excess of from 300 to 700, preferably 350 to 400, mol % of hydrogen fluoride per trichloromethyl equivalent is added to the starting material V in an autoclave, and the mixture is then stirred for from 10 minutes to about 10 hours. The reaction rate can be increased in the same way as described for the use of antimony trifluoride, i.e. by addition of a catalyst such as antimony pentachloride. A reaction time of about 4 hours is generally sufficient. After release of pressure and removal of volatile constituents, working up is carried out as described.

The novel 2-amino-4-fluoroalkoxy-1,3,5-triazines I are valuable intermediates for preparing crop protection agents. They can be subjected to the process described in German Application P 40 24 754 (O.Z. 0050/41800) of the same date, for example 2-amino-4-fluoro-6-trifluoromethoxy-1,3,5-triazine can be reacted with methanol to give 2-amino-6-methoxy-4-trifluoromethoxy-1,3,5-triazine which reacts with 2-carbomethoxybenzenesulfonyl isocyanate to give herbicidal sulfonylureas. However, they can also be reacted directly with the said isocyanate to give herbicidal sulfonylureas.

EXAMPLES

I. Examples of the preparation of the precursors (cf. German Application P 40 24 755 (O.Z. 0050/41798) of the same date)

Example I.1

2,4-Difluoro-6-trichloromethoxy-1,3,5-triazine

A stream of gaseous chlorine was passed into a mixture of 300 g (2.041 mol) of 2,4-difluoro-6-methoxy-1,3,5-triazine and 0.3 g of α,α'-azoisobutyronitrile at 130° C. with UV irradiation in such a way that the temperature reached 140°–145° C. within 2 hours. The progress of the reaction was checked by NMR spectroscopy and then chlorine was passed in at 135°–140° C. (external heating) for a further 3 hours.

The precipitate was removed by filtration with suction and the filtrate was distilled under reduced pressure to yield 444 g (87% of theory) of the title compound of boiling point 40°–46° C./0.3 mbar.

Example I.2

2,4-Difluoro-6-trifluoromethoxy-1,3,5-triazine

Half of 210 g (0.838 mol) of 2,4-difluoro-6-trichloromethoxy-1,3,5-triazine was added to a stirred mixture of 187.4 g (1.048 mol) of antimony trifluoride and 35.2 g (0.117 mol) of antimony pentachloride in such a way that the initial temperature of 110° C. rose to 125° C.; when reflux ceased, external heating was necessary while addition was continued. The mixture was stirred at 125°-130° C. for one hour, and a fraction boiling at 100°-105° C. was removed by distillation through a 25 cm packed column. After the reaction subsided, the remaining half of the trichloromethoxy compound was added dropwise within 30 minutes, and the fraction boiling at 100°-105° C. was continuously distilled out. The total reaction time was 3 hours. 134.4 g (79.8% of theory) of the title compound were obtained with $n_D^{24} = 1.3650$.

Example I.3

6-Chlorodifluoromethoxy-2,4-difluoro-1,3,5-triazine 210 g (0.838 mol) of 2,4-difluoro-6-trichloromethoxy-1,3,5-triazine were added within 10 minutes to 110 g (0.615 mol) of antimony trifluoride while stirring at 110° C. After addition of 3/4 of 9.38 g (0.0313 mol) of antimony pentachloride, the mixture was heated to 145° C. and stirred for 1 hour. The remaining catalyst was added, and the mixture was stirred for a further 2 hours while a fraction boiling at 95°-105° C. was obtained through a 30 cm packed column: 20 g (11.8% of theory) of 2,4-difluoro-6-trifluoromethoxy-1,3,5-triazine. The residue was distilled without a column to yield 94.8 g (52% of theory) of the title compound of boiling point 125°-130° C.; $n_D^{24} = 1.4042$.

Example I.4

2,4-Dichloro-6-trifluoromethoxy-1,3,5-triazine 52 g (0.183 mol) of 2,4-dichloro-6-trichloromethoxy-1,3,5-triazine were added within 5 minutes to a stirred mixture of 40.9 g (0.229 mol) of antimony trifluoride and 7.03 g (0.0234 mol) of antimony pentachloride at 90° C., during which the temperature rose to 180° C. The mixture was then stirred at 170°-180° C. for 20 minutes, after which the crude product was distilled out at 90°-103° C./70 mbar. Another distillation yielded 32.3 g (75.5% of theory) of the title compound of boiling point 165°-173° C.

II. Preparation of the compounds I according to the invention

Example II.1

2-Amino-4-fluoro-6-trifluoromethoxy-1,3,5-triazine 4.4 g (0.259 mol) of gaseous ammonia were passed over the course of 45 minutes into a stirred mixture of 26.0 g (0.1293 mol) of 2,4-difluoro-6-trifluoromethoxy-1,3,5-triazine and 100 ml of tetrahydrofuran at −70° to −65° C. The mixture was then stirred for 2 hours at −70° C. and overnight while warming to 22° C. The residue from concentration under reduced pressure was stirred with water, filtered off with suction and washed. Drying yielded 22 g (85.9% of theory) of the title compound of melting point 138°-139° C.

Example II.2

2,4-Bismethylamino-6-trifluoromethoxy-1,3,5-triazine
and
2-methylamino-4-fluoro-6-trifluoromethoxy-1,3,5-triazine 5.9 g (0.189 mol) of methylamine were passed over the course of 30 minutes into a stirred mixture of 19.0 g (0.0945 mol) of 2,4-difluoro-6-trifluoromethoxy-1,3,5-triazine and 100 ml of diethyl ether at −70° C. The mixture was stirred for 2 hours at −70° C. and overnight while warming to 22° C. The residue from concentration under reduced pressure was taken up in methylene chloride and washed with water. The solution was dried and chromatographed through a silica gel column. The first two fractions contained 5.0 g (25% of theory) of 2-methylamino-4-fluoro-6-trifluoromethoxy-1,3,5-triazine of melting point 68°-72° C., and fractions 4-7 yielded 10.7 g (51% of theory) of less soluble 2,4-bismethylamino-6-trifluoromethoxy-1,3,5-triazine of melting point 150°-152° C.

Example II.3

2-Amino-4-chlorodifluoromethoxy-6-fluoro-1,3,5-triazine
and
2,4-diamino-6-chlorodifluoromethoxy-1,3,5-triazine 7.8 g (0.46 mol) of ammonia were passed over the course of 45 minutes into a stirred mixture of 50.0 g (0.23 mol) of 2,4-difluoro-6-chlorodifluoromethoxy-1,3,5-triazine and 150 ml of tetrahydrofuran at −70° C. The mixture was stirred for 2 hours at −70° C. and overnight while warming to 22° C. It was concentrated under reduced pressure, washed with water and dried. The product was then loaded in methylene chloride onto a silica gel column and eluted with the same solvent. Fractions 1-8 yielded 21.5 g (43.6% of theory) of 2-amino-4-fluoro-6-chlorodifluoromethoxy-1,3,5-triazine of melting point 131°-133° C.

Washing with ethyl acetate then yielded in fractions 9-14 the less soluble 2,4-diamino-6-chlorodifluoromethoxy-1,3,5-triazine (11.2 g, 23% of theory) of melting point 114° C.

Example II.4

2-Chlorodifluoromethoxy-4-fluoro-6-methylamino-1,3,5-triazine
and
2,4-bismethylamino-6-chlorodifluoro-methoxy-1,3,5-triazine 5.2 g (0.166 mol) of methylamine were passed over the course of 20 minutes into a stirred mixture of 18.1 g (0.083 mol) of 4-difluorochloromethoxy-2,6-difluoro-1,3,5-triazine and solvent at −70° C. The mixture was stirred for 2 hours at −70° C. and overnight while warming to 22° C. It was concentrated under reduced pressure, taken up in methylene chloride, washed with water and dried. Chromatography on silica gel yielded in the initial fractions 5.5 g (29% of theory) of 2-chlorodifluoromethoxy-4-fluoro-6-methylamino-1,3,5-triazine of melting point 62°-64° C. Subsequent fractions yielded 8.7 g (44% of theory) of 2,4-bismethylamino-6-chlorodifluoromethoxy-1,3,5-triazine of melting point 118°-120° C.

III. Conversion of the 1,3,5-triazines into herbicidal sulfonylurea derivatives

Example III.1

2-Amino-4-methoxy-6-trifluoromethoxy-1,3,5-triazine 9.1 g (0.0505 mol) of 30% strength sodium methylate were added over the course of 15 minutes to a stirred mixture of 10 g (0.0505 mol) of 2-amino-4-fluoro-6-trifluoromethoxy-1,3,5-triazine and 100 ml of methanol at 0° C. The mixture was stirred at 0° C. for one hour and then concentrated under reduced pressure, taken up in methylene chloride and extracted with water. Drying and concentration yielded 10.5 g (99% of theory) of the title compound of melting point 96°-101° C.

Example III.2

2-Amino-4-chlorodifluoromethoxy-6-methoxy-1,3,5-triazine 8.4 g (0.0466 mol) of 30% strength sodium methylate were added over the course of 15 minutes to a stirred mixture of 10 g (0.0466 mol) of 2-amino-4-chlorodifluoromethoxy-6-fluoro-1,3,5-triazine and 100 ml of methanol at 0° C. The mixture was stirred at 0° C. for one hour and then concentrated under reduced pressure, taken up in methylene chloride and extracted with water. Drying and concentration yielded 10.4 g (98.5% of theory) of the title compound of melting point 109°–111° C.

Example III.3

2-Amino-4-ethoxy-6-trifluoromethoxy-1,3,5-triazine 2.3 g (0.093 mol) of 97% sodium hydride were added a little at a time to 300 ml of ethanol at 20°–35° C. and dissolved by stirring for 15 minutes. Then, while stirring at 0° C., 18.5 g (0.093 mol) of 2-amino-4-fluoro-6-trifluoromethoxy-1,3,5-triazine were added over the course of 10 minutes, and the mixture was stirred at 0° C. for 1 hour and at 22° C. overnight. The residue from concentration under reduced pressure was taken up in methylene chloride, extracted with water and dried. Concentration yielded 17.9 g (85.9% of theory) of the title compound of melting point 69°–71° C.

Example III.4

2-Amino-4-chlorodifluoromethoxy-6-ethoxy-1,3,5-triazine 1.2 g (0.0466 mol) of 97% sodium hydride were added a little at a time to 150 ml of ethanol at 20°–35° C. and dissolved by stirring for 15 minutes. Then, while stirring at 0° C., 10.0 g (0.046 mol) of 2-amino-4-chlorodifluoromethoxy-6-fluoro-1,3,5-triazine were added, and the mixture was stirred at 0° C. for 1 hour and at 22° C. overnight. The residue from concentration under reduced pressure was taken up in methylene chloride, extracted with water and dried. Concentration yielded 10.6 g (94.6% of theory) of the title compound of melting point 63°–65° C.

Example III.5

2-Amino-4-methylamino-6-trifluoromethoxy-1,3,5-triazine 3.5 g (0.111 mol) of methylamine were passed over the course of 20 minutes into a stirred solution of 11 g (0.055 mol) of 2-amino-4-fluoro-6-trifluoromethoxy-1,3,5-triazine in 150 ml of tetrahydrofuran at 0° C. The mixture was stirred at 0° C. for one hour and at 22° C. overnight. It was then concentrated under reduced pressure, stirred with water and dried. 10.8 g (93.1% of theory) of the title compound of melting point 155°–157° C. (decomposition) were obtained.

Example III.6

2-Amino-4-chlorodifluoromethoxy-6-methylamino-1,3,5-triazine 2.9 g (0.0932 mol) of methylamine were passed over the course of 20 minutes into a stirred solution of 10 g (0.0466 mol) of 2-amino-4-chlorodifluoro-methoxy-6-fluoro-1,3,5-triazine in 150 ml of diethyl ether at 0° C. The mixture was stirred at 0° C. for one hour and at 22° C. overnight. Washing with water, drying and concentration yielded 9.4 g (89.5% of theory) of the title compound of melting point 143° C. (decomposition).

Example III.7

2-Amino-4-dimethylamino-6-trifluoromethoxy-1,3,5-triazine 5.0 g (0.111 mol) of dimethylamine were passed over the course of 20 minutes into a stirred solution of 11 g (0.055 mol) of 2-amino-4-fluoro-6-trifluoro-methoxy-1,3,5-triazine in 150 ml of tetrahydrofuran at 0° C. The mixture was stirred at 0° C. for one hour and at 22° C. overnight. Concentration, washing with water and drying yielded 9.9 g (80.7% of theory) of the title compound of melting point 114°–118° C. (decomposition).

Example III.8

2-Amino-4-chlorodifluoromethoxy-6-dimethylamino-1,3,5-triazine 4.2 g (0.093 mol) of dimethylamine were passed over the course of 20 minutes into a stirred solution of 10 g (0.0466 mol) of 2-amino-4-chlorodifluoro-methoxy-6-fluoro-1,3,5-triazine in 150 ml of diethyl ether at 0° C. The mixture was stirred at 0° C. for one hour and at 22° C. overnight. Washing with water, drying and concentration yielded 9.8 g (87.8% of theory) of the title compound of melting point 130°–133° C. (decomposition).

Example III.9

Methyl 2-(4-methoxy-6-trifluoromethoxy-1,3,5-triazin-2-ylaminocarbonylaminosulfonyl)benzoate 3.6 g (0.015 mol) of 2-carbomethoxybenzenesulfonyl isocyanate in 4 ml of 1,2-dichloroethane were added over the course of 5 minutes to a stirred mixture of 3.15 g (0.015 mol) of 2-amino-4-methoxy-6-trifluoromethoxy-1,3,5-triazine and 150 ml of 1,2-dichloroethane at 22° C., and the mixture was stirred at 22° C. for 12 hours. It was then concentrated under reduced pressure and crystallized using 1:1 methyl tert-butyl ether/petroleum ether, and the product was filtered off with suction and washed with petroleum ether to yield 5.1 g (75.4% of theory) of the title compound of melting point 149° C. (decomposition).

Example III.10

Sodium salt of methyl 2-(4-methoxy-6-trifluoromethoxy-1,3,5-triazin-2-ylaminocarbonylaminosulfonyl)benzoate 1.8 g (0.004 mol) of the compound from Example III.9 were suspended in 30 ml of methanol and, while stirring at 10°–15° C., 0.72 g (0.004 mol) of 30% strength sodium methylate solution was added. The clear solution was stirred for 10 minutes and then concentrated under reduced pressure, resulting in 1.9 g (100% of theory) of the title compound of melting point 118° C. (decomposition).

Example III.11

Ethyl 2-(4-methylamino-6-trifluoromethoxy-1,3,5-triazin-2-ylaminocarbonylaminosulfonyl)benzoate 3.1 g (0.012 mol) of 2-carboethoxybenzenesulfonyl isocyanate in 3 ml of methylene chloride were added over the course of 10 minutes to a stirred mixture of 2.5 g (0.012 mol) of 2-amino-4-methylamino-6-trifluoromethoxy-1,3,5-triazine and 150 ml of methylene chloride at

We claim:

1. A substituted 2-amino-4-fluoroalkoxy-1,3,5-triazine of the formula I

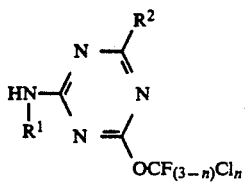

where
$R^1$ is hydrogen, $C_1$-$C_4$-alkyl, $C_3$-$C_6$-alkenyl or $C_3$-$C_4$-alkynyl;
$R^2$ is hydrogen, halogen, $C_1$-$C_4$-haloalkyl, trifluoromethoxy or chlorodifluoromethoxy and
n is 1.

2. A process for preparing a 2-amino-4-fluoroalkoxy-1,3,5-triazine of the formula I

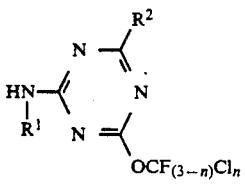

where
$R^1$ is hydrogen, $C_1$-$C_4$-alkyl, $C_3$-$C_6$-alkenyl or $C_3$-$C_4$-alkynyl;
$R^2$ is hydrogen, halogen, $C_1$-$C_4$-haloalkyl, trifluoromethoxy or chlorodifluoromethoxy and
n is 0 or 1,
which comprises reacting a 2-halo-1,3,5-triazine of the formula II

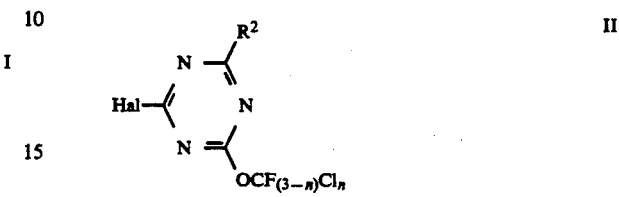

where Hal is fluorine, chlorine, bromine or iodine, and $R^2$ and n have the abovementioned meanings, with an amine of the formula III

where $R^1$ has the abovementioned meaning, in the presence or absence of an additional organic base.

3. A process as claimed in claim 2, wherein ammonia is used as amine.

4. A process as claimed in claim 2, wherein methylamine is used as amine.

5. A process as claimed in claim 2, wherein the reaction is carried out at from $-80°$ to $40°$ C.

6. 2-Amino-4-chlorodifluoromethoxy-6-fluoro-1,3,5-triazine.

7. 2-Chlorodifluoromethoxy-4-fluoro-6-methylamino-1,3,5-triazine.

* * * * *